United States Patent [19]

Gersdorff

[11] Patent Number: 4,728,327
[45] Date of Patent: Mar. 1, 1988

[54] MIDDLE-EAR PROSTHESIS

[76] Inventor: Michel Gersdorff, 24, Avenue des Myrtilles, B-1950 Kraainem, Belgium

[21] Appl. No.: 3,088

[22] Filed: Jan. 14, 1987

[30] Foreign Application Priority Data

Jan. 27, 1986 [FR] France ................................ 86 01073

[51] Int. Cl.$^4$ ................................................. A61F 2/18
[52] U.S. Cl. ........................................................ 623/10
[58] Field of Search .............................. 623/10, 16, 18

[56] References Cited

U.S. PATENT DOCUMENTS

| | | | |
|---|---|---|---|
| 4,130,905 | 12/1978 | Mercandino | 623/10 |
| 4,169,292 | 10/1979 | Grote | 623/10 |
| 4,510,627 | 4/1985 | Treace et al. | 623/10 |
| 4,624,672 | 11/1986 | Lenkauskas | 623/10 |

FOREIGN PATENT DOCUMENTS

WO83/03350 10/1983 PCT Int'l Appl. ................. 623/16

OTHER PUBLICATIONS

Search Report FR 86 01 073 including 1 annex page.

*Primary Examiner*—Ronald L. Frinks
*Attorney, Agent, or Firm*—Ladas & Parry

[57] ABSTRACT

The invention relates to a medical prosthesis.

This is a middle-ear prosthesis (16) provided with a means (23) of fastening to the tympanic frame (24), a flexible suspension means (22), and a means of transmitting sound between the tympanic membrane (3) and the oval window, the transmission means comprising an arm (17) representing the malleus (4) and connected to a second arm (19) representing the incus (6) and connected to the stapes (8) or to a columella (21) representing it.

The suspension to the tympanic frame (24) ensures better compliance and the independent articulation to the tympanic membrane (3), on the one hand, and to the base (10) of the steps (8), on the other hand, effects a diminution of impedance, thus giving better transmission of sound between the external ear and the inner ear.

14 Claims, 4 Drawing Figures

MIDDLE-EAR PROSTHESIS

BACKGROUND OF THE INVENTION

1. Field of the Invention

The present invention relates to a middle-ear prosthesis.

The natural mechanism for the transmission of sonic vibrations from the tympanum to the inner ear functions via the ossicular chain of the middle ear, consisting of three articulated ossicles—the malleus, the incus and the stapes, which amplify the vibrations of the tympanum for transmission of sound to the inner ear. The fenestra of the vestibule, in which the stapes (the smallest of the ossicles) lies, provides communication between the middle ear and the inner ear. The assembly comprising the tympanum and the chain of ossicles is commonly called the "tympano-ossicular complex".

Numerous pathologies of the middle ear (chronic otitis media in different forms, injuries, sequelae of previous operations) may result in dysfunction of the tympano-ossicular complex. This dysfunction entails a hearing impairment in the form of conduction deafness, that is to say impairment of the auditory function characterized by failure to achieve correct transmission of the sound message propagated from the external ear to the inner ear.

The middle ear functions essentially as an acoustic impedance transformer. If it cannot perform this function, the cochlear input signal is diminished and so-called conduction deafness results.

Such conduction deafness is principally associated with damage to the tympanum (perforation of the tympanum or with injury to the ossicular chain (ankylosis or ossicular lysis).

If the tympano-ossicular complex were entirely absent, the sound waves transmitted through the atmosphere would, without transition, encounter the base of stapes, in the fenestra of the vestibule, and would be reflected.

As a result, only a very small part (about one thousandth) of the sonic energy would be transmitted to the liquid of the inner ear.

This would mean that the patient would suffer a diminution of sensation of sound intensity perceived in the labyrinth of the inner ear. This diminution can be expressed as a loss in decibels.

It should be noted that the reconstruction of the various osseous parts of the middle or external ear is possible by means of ossicular alloplasty (ossicle taken from a donor) or by means of autoplasty (removal of one of the patient's ossicles, remodelling and restoration of tympano-ossicular continuity), or, more recently, by fitting a prosthesis made of a so-called biocompatible material. In recent years use has in particular been made of porous polyethylene (such as the porous polyethylene marketed under the trade mark Proplast ®) or of biocompatible ceramics, particularly bioactive biocompatible ceramics (such as that marketed under the trade mark Ceravital ®).

2. Description of the prior art

The reconstruction of the sound transmission mechanism in the middle ear by the implantation of biocompatible prostheses in well known.

It is in fact known to remedy different types of conduction deafness by replacing different parts of the ear, depending on the defect from which the patient suffers. The osseous frame of the external ear, the annulus surrounding the tympanum, the tympanic membrane itself, and each of the three ossicles of the ossicular chain can thus be replaced or repaired.

Depending on circumstances and on the type of surgical operation carried out, different categories of prostheses can be distinguished, for the production of which various materials may be used.

In Grote's U.S. Pat. No. 4,169,292 a prosthesis is described which is intended to replace the entire structure of the ear from the osseous canal of the external ear to the fenestra of the vestibule, which determines the frontier between the middle ear and the inner ear.

That part of Grote's prosthesis which is intended to replace the ossicular chain is fastened to an artificial ring, which in turn is joined to a tube replacing the osseous canal.

This type of prosthesis cannot be used if only the ossicular chain is defective or missing.

It is also known to reconstruct only the tympano-ossicular complex, or only the ossicular chain of the middle ear, or only a part of that chain.

A reconstruction of this kind can be made in the event of total excision. In this case the prosthesis is placed in a position different from that occupied by the natural ossicular chain in the cavity of the middle ear.

This is the case, for example, with Mercandino's U.S. Pat. No. 4,130,905, which describes a prosthesis consisting of a single piece replacing the entire ossicular chain, the position of the neotympanum being different from the normal position of the tympanum.

The use of a prosthesis of this kind entails a surgical operation completely changing the structure of the middle ear.

It is also known to reconstruct the ossicular chain of the middle ear when the position of the tympanum (naturel or neoformed) is retained.

There are two forms of prosthesis for the ossicular chain. When the stapes is intact, the prosthesis, which is then said to be partial, is fitted between the tympanum (or neotympanum) and the apex of the stapes. When only the base of the stapes is retained, the prosthesis is said to be total and is fitted directly between the tympanum (or neotympanum) and the base.

Total prostheses in use at the present time are generally prostheses functioning in the form of columellae, that is to say the entire ossicular chain (malleus, incus, stapes) is replaced by a single linear prosthesis interposed directly between the tympanum (or neotympanum) and the base of the stapes.

Examples of prostheses of this kind are described in U.S. Pat. Nos. 3,909,852 and 4,052,754 (Homsy), in 4,287,616 (Heimke et al.), and in 4,281,419 (Treace).

In the physical aspect, columellar type prostheses transmit sound directly from the tympanum to the base of the stapes and the tympanum is in direct contact with the prostheses.

In the normal ossicular chain the malleus is longer than the incus and is articulated to the latter by means of the incudomalleal joint. This has the consequence that this part of the chain serves as a lever arm permitting amplification of sound. This function is not served by columellar prostheses.

Furthermore, a second joint, known as the incudostapedial joint, exists between the malleus and the stapes in the normal chain.

The function of the joints is very important, because at one and the same time they permit smooth, progressive sound transmission and provide amplification through the lever arm system. This is not so in the case of columellar prostheses.

SUMMARY OF THE INVENTION

In order to obviate the shortcomings of total linear prostheses used hitherto, and to restore the advantages offered by the normal ossicular chain in the sound transmission mechanism, the Applicant has developed an articulated prosthesis effecting non-linear sound transmission from the tympanum to the stapes. The prosthesis according to the invention may be used as a partial or total prosthesis, depending on whether the stapes is retained intact or only its base remains.

It may also be placed in the ear whether the bony parts of the latter are natural or have themselves been entirely or partially reconstructed. Similarly, the prosthesis according to the invention can function whether the tympanum is intact or replaced by a neotympanum.

The present invention therefore relates to a middle-ear prosthesis comprising a fastening means insertable into the bony part of the middle ear, a flexible suspension means which is orientable and adjustable, and a means of transmitting sound between the tympanic membrane and a constituent part of the stapes, the transmission means being connected to said fastening means by said suspension means and said sound transmission means comprising a first arm representing the malleus and making contact with the tympanic membrane, and a second, shorter arm representing the incus. The two arms, joined together by a connecting member, are directed in two planes parallel to one another and, viewed in a direction at right angles to these planes, are seen to form an acute angle between them. The free end of the second arm is connected to a constituent part of the stapes.

The free end of the second arm may be connected to the stapedial arch of the stapes by a second connecting member, and forms between the arm and the arch an angle close to a right angle.

When the branches of the stapes are not retained, but only its base remains, as is frequently the case, the second arm is connected to a rod or columella whose free end makes contact with the base of the stapes. The columella is therefore connected to the second arm by a second connecting member, the second arm by a second connecting member, the second arm and the columella forming between them an angle close to a right angle.

In the latter case the prosthesis according to the invention is a total prosthesis.

In cases where the stapedial arch of the stapes is retained, the prosthesis according to the invention is a partial prosthesis.

The first and/or the second connecting member may be either fixed or be orientable and adjustable.

In the prosthesis according to the present invention the tympanum is in contact only with the first arm, which represents the malleus. The stapes, when it is retained intact, is in contact with the second arm, which is independent of the first. When only the base is retained, the prosthesis is in contact with the latter by way of a columella carried by the end of the second arm.

In addition, the ossicular prosthesis may be suspended on a bony part of the middle ear by inserting the fastening means in the tympanic frame, the auditory meatus, or in any other position in the middle ear, depending on the surgical technique employed. The fastening means may optionally be inserted into an artificially created part of the ear.

The function of the prosthesis suspension means is similar to that served by the suspensory ligaments of the natural ossicular chain.

The prosthesis according to the invention permits smooth transmission of sound from the tympanum to the base of the stapes; the first arm, representing the malleus, vibrates with the tympanum, and the second arm, representing the incus, causes the base of the stapes to vibrate.

The structure of the prosthesis is such that it permits non-rigid, flexible suspension approximating to physiological conditions.

The absence of contact between that part of the prosthesis which fits the tympanum and that which fits the stapes (or its base) reduces the impedance of the transmission system through the lever arm principle.

The fact that the prosthesis is suspended on a bony part of the ear, independently of the tympanic membrane, ensures a good compliance effect.

That part of the prosthesis according to the invention wich replaces the ossicles and also the plate (fastening means intended to be fixed, for example, in the tympanic frame) are made of so-called biocompatible material, particularly bioactive ceramic material, for example a bioceramic sold under the trade mark Ceravital ®. The suspension means is orientable and adjustable and can be made of a biocompatible synthetic material or may consist of a wire, for example of stainless steel.

In order to achieve optimum contact between the columella or rod of the total prosthesis and the base of the stapes, and in order to hold this rod in the middle of the base, a stabilizer, such as that described in the applicant's copending application Ser. No. 003,082 of the same date, is preferably placed in position on the base.

When the tympanic membrane is affected, most otological surgeons replace it at the present time by grafting a fragment of temporal fascia. It is also possible to use a tympanic allograft (from a preserved human tympanum) or a tympanic zenograft (for example from a calf's jugular vein).

In the case of replacement of the tympanic membrane by a neotympanum, the prosthesis according to the invention will bear against it and will serve the same function as in the case of a natural membrane.

In the same way, when the bony part of the middle ear is damaged, it is possible to insert the fastening means of the prosthesis according to the invention in an artificially created bony part.

BRIEF DESCRIPTION OF THE DRAWINGS

One example of construction of the prosthesis according to the invention is described below with reference to the accompanying drawings, in which like reference numerals related to like elements.

DETAILED DESCRIPTION OF THE INVENTION

Figure 1:
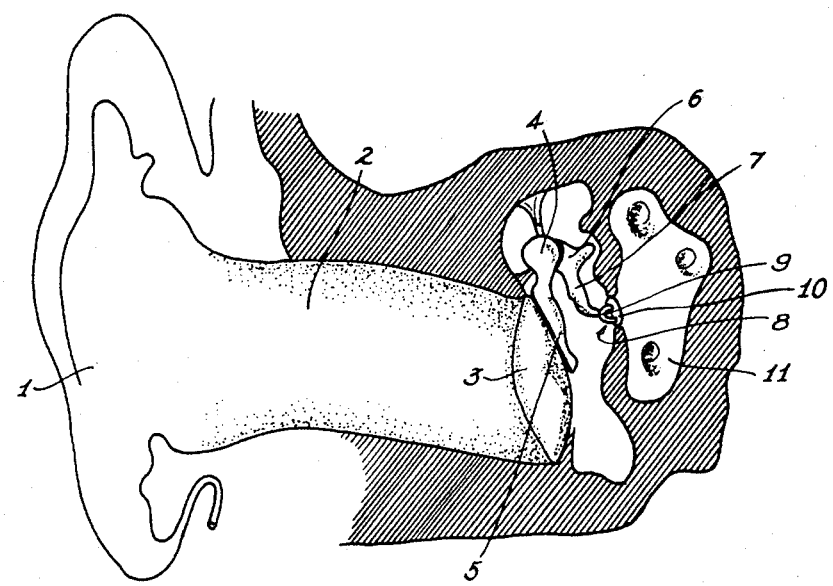
FIG. 1 is a schematic elevation, partly in section, of the ear (external, middle and inner)

FIG. 1 shows the auricle 1 of the external ear, the external auditory meatus 2, the tympanic membrane 3, and the ossicular chain of the middle ear, consisting of three articulated ossicles: the malleus 4 with its long process (or handle) 5, the incus 6 with its long process 7, and the stapes 8 with its stapedial arch 9 and its base 10, and finally the inner ear 11.

Figure 2:
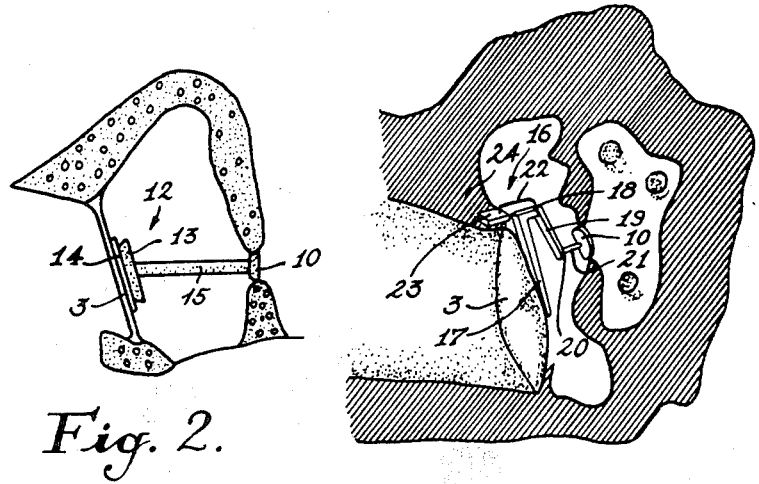
FIG. 2 is a schematic elevation of the middle ear, in which the ossicles are replaced by a columellate prosthesis according to U.S. Pat. No. 4,510,627.

FIG. 2 shows a total middle-ear prosthesis 12 consisting on the one hand of a widened round head 13 adhering to the tympanic membrane 3 by means of a cartilage 14, and on the other hand of an elongate rod (columella) 15 bearing against the base 10 of the stapes 8.

Figure 3:
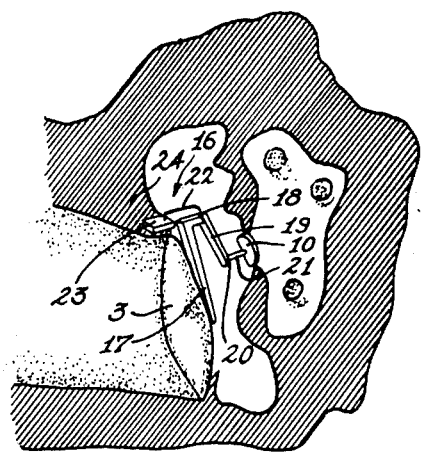
FIG. 3 is a schematic elevation of the middle ear, in which the ossicles are replaced by a total prosthesis according to the present invention.
Figure 4:
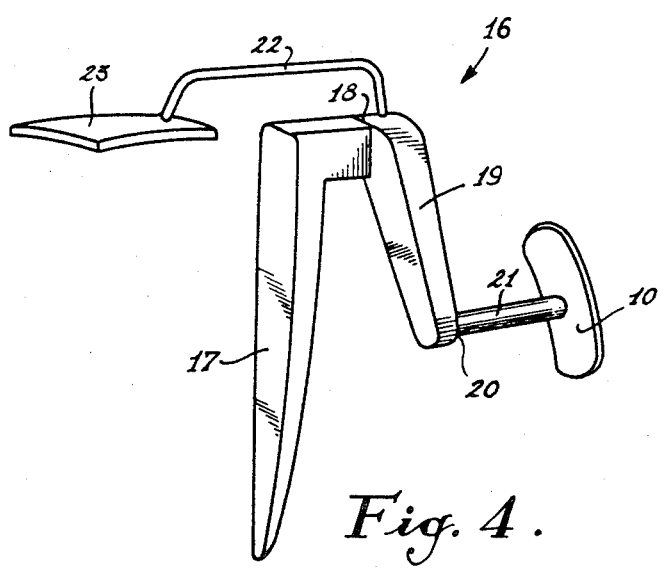
FIG. 4 is an elevation on a larger scale of the total prosthesis according to the present invention, with its fastening means and suspension means.

FIGS. 3 and 4, show a total prosthesis 16 according to the invention, comprising a first arm 17 representing the malleus 4 and making contact with the tympanic membrane 3. The first arm 17 is connected at an acute angle to one end of a second arm 19 by the connecting member 18. The second arm 19 representing the incus 6 is connected at its other end, at an angle close to a right angle, to a rod (columella) 21 by the second connecting member 20. The free end of the columella 21 makes contact with the base 10 of the stapes 8. It should be noted that the first arm 17 is longer than the second arm 19. The entire prosthesis 16 is suspended by means of the wire 22, of metal or any other biocompatible synthetic material, on the plate 23 fixed in the tympanic frame 24. This wire 22 is orientable and adjustable in such a manner that if the tympanic frame 24 is damaged, the plate 23 can be fixed to the auditory meatus or to any other natural or artificial part of the middle ear, depending on the surgical technique employed. The connecting members 18 and 20 may also be orientable or adjustable.

It will readily be understood that in comparison with the columella prosthesis shown in FIG. 2 the prosthesis 16 according to the invention (FIGS. 3 and 4) offers indisputable adavantages.

The arm 17 does not adhere rigidly and inseparably to the tympanic membrane 3. It is fixed, for example to the tympanic frame 24, by means of a flexible suspension, namely the wire 22 of metal (or other biocompatible material), just as the malleus 4 of a natural ear is suspended in the middle ear cavity by means of suspensory ligaments.

On the other hand, instead of making direct, rigid connection 15 between the tympanic membrane 3 and the base 10 of the stapes, as is the case in known prosthesis 12, the prosthesis 16 of the invention includes two connecting members 18 and 20, which thus separate the contact with the tympanic membrane 3 from the contact with the base 10. This ensures more physiological transmission of tympanic vibrations to the stapes 8, and thence to the inner ear 11.

The presence of the prosthesis 16 in the middle ear permits transmission of sonic energy in such a manner that the latter is not reflected by the base 10 of the stapes 8 at the oval window, and that there is minimum loss of sensation of sonic energy.

The spatial structure of the prosthesis 16 serves an important function, inasmuch as the shape and position of the centers of gravity of the arm 17 replacing the malleus 4 and of the arm 19 replacing the incus 6 play an important part in the transmission of sound.

A depression of the tympanic membrane 3 has the consequence of driving the base 10 into the perilymph fluids of the inner ear 11. The incident sound thus entails in the middle ear a succession of complex oscillations of the prosthesis 16, which leads to a succession of blows applied to the base 10 of the stapes 8.

The prosthesis 16 also permits a phase displacement of the waves between the oval window and the round window, such as is indispensable for the physiology of the cochlea. Because of its mass and its static strength, the ossicular chain in fact transmits to the oval window a wave which has undergone phase displacement in relation to the wave reaching the round window.

As the area of the base 10 amounts on the average to 2.5 square millimeters and that of the vibrating prt of the tympanic membrane 3 to 35 square millimeters, this means that the energy passing through the ossicular chain is concentrated on the base 10, thereby increasing the sensation of sonic intensity by about 23 dB. In fact, $10 \log (35/2.5)^2 = 10 \log 14_2 = 20 \log 14 = 23$ dB.

This partial recuperation of sonic intensity sensation because of the presence of the tympanoossicular complex exists in the normal ear and can also exist in the case of total prostheses of the columellate type, provided that the ratio of areas of contact is retained.

An additional proportion of sonic intensity sensation can also be recovered at the oval window with the aid of the prosthesis 16 according to the invention. This prosthesis serves as a lever, as the result of which the pressure due to the translatory movement is greater at the base 10 than at the tympanic membrane 3.

This is due to the fact that the arm 17 making contact with the tympanic membrane 3 is longer than the arm 19 making contact with the stapes 8 (or, by way of the columella 21, making contact with the base 10 of the stapes 8). The displacement of the end of the short arm 19, and therefore also of the base 10 of the stapes 8, will therefore be less than that of the end of the long arm 17, but this reduction of the amplitude of displacement is accompanied by increasing pressure.

The amplitude of the displacement of the base 10 is estimated at from $10^{-11}$ to $10^{-12}$ centimeters.

Because of the lever action of the prosthesis 16, the pressure exerted on the base 10 is equal to 1.31 times the pressure exerted on the tympanic membrane 3, and this results in the additional recuperation of 3 dB. In fact, $10 \log ((1.31/1)^2)\ 20 \log 1.31 = 3$ dB.

Consequently, the prosthesis 16 according to the invention makes it possible to recover about 26 dB in comparison with the case where the tympano-ossicular complex is absent, that is to say 3 dB more than known columellate prostheses.

I claim:

1. A prosthesis (16) for in vivo implantation in the middle ear cavity for transmitting sound between the tympanic membrane (3) and a constituent part of the stapes (8), which prosthesis (16) comprises a sound transmission means, a fastening means (23) and a flexible elongated suspension means (22), said sound transmission means comprising a first arm (17) representing the malleus (4) adapted to make contact with the tympanic membrane (3) and a second, shorter arm (19) representing the incus (6), the two arms (17, 19), joined together by a connecting member (18), being directed in two planes parallel to one another and being seen to form an acute angle between them when viewed in a direction at right angles to said planes, the free end of the second arm (19) being adapted to be connected to a constituent part of the stapes (8), said fastening means (23) being adapted to be inserted in the middle ear cavity into a bony part of the ear, said suspension means (22) being orientable and adjustable, said sound transmission means being connected to said fastening means (23) by said suspension means (22), one end of said suspension means (22) being connected to said fastening means (23) and the other end of said suspension means (22) being connected to the sound transmission means at a point close to the junction of the two arms (17, 19).

2. A prosthesis as claimed in claim 1, in which the fastening means (23) is adapted to be inserted into the auditory meatus.

3. A prosthesis as claimed in claim 1, in which the fastening means (23) is adapted to be inserted into the tympanic frame (24).

4. A prosthesis as claimed in claim 1, in which the connecting member (18) is fixed.

5. A prosthesis as claimed in claim 1, in which the connecting member (18) is orientable and adjustable.

6. A prosthesis as claimed in claim 1, in which the free end of the second arm (19) is adapted to be connected to the stapedial arch (9) of the stapes (8) by a second connecting member (20) and is adapted to form between the second arm (19) and the arch (9) an angle close to a right angle.

7. A prosthesis as claimed in claim 1, in which the free end of the second arm (19) is connected to a columella (21) whose free end is adapted to make contact with the base (10) of the stapes (8), said columella (21) being connected to the second arm (19) by a second connecting member (20), and the second arm (19) and the columella (21) forming between them an angle close to a right angle.

8. A prosthesis as claimed in claim 6 in which the second connecting member (20) is fixed.

9. A prosthesis as claimed in claim 7 in which the second connecting member (20) is fixed.

10. A prosthesis as claimed in claim 7 in which the second connecting member (20) is orientable and adjustable.

11. A prosthesis as claimed in claim 1, in which the means (23) adapted to be fastened in the middle ear cavity into a bony part of the ear and the sound transmission means are of biocompatible ceramic material.

12. A prosthesis as claimed in claim 1, in which the means (23) adapted to be fastened in the middle ear cavity into a bony part of the ear and the sound transmission means are of bioactive biocompatible ceramic material.

13. A prosthesis as claimed in claim 1, in which the flexible elongated suspension means (22) is orientable and adjustable and is made of a biocompatible synthetic material.

14. A prosthesis as claimed in claim 1, in which the flexible elongated suspension means (22) is orientable and adjustable and consists of a metal wire.

* * * * *